US009597376B2

(12) United States Patent
Francone et al.

(10) Patent No.: US 9,597,376 B2
(45) Date of Patent: Mar. 21, 2017

(54) LIPOPROTEIN LIPASE FOR TREATMENT OF HYPERTRIGLYCERIDEMIC-RELATED CONDITIONS INCLUDING ACUTE PANCREATITIS

(71) Applicant: Shire Human Genetic Therapies, Inc., Lexington, MA (US)

(72) Inventors: Omar L. Francone, East Lyme, CT (US); Lin Guey, Watertown, MA (US); Kevin Holmes, Belmont, MA (US); Bruce Tangarone, Hampstead, NH (US); Matthew Traylor, Cambridge, MA (US); Lenore von Krusenstiern, Brookline, MA (US); Tracy Dowie, Lexington, MA (US); Lieh Yoon Low, Lexington, MA (US); Bohong Zhang, Lexington, MA (US); Muthuraman Meiyappan, Lexington, MA (US); Angela Norton, Reading, MA (US); Bettina Strack-Logue, Somerville, MA (US); Dianna Lundberg, Brentwood, NH (US); Michael F. Concino, Bolton, MA (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

(21) Appl. No.: 14/830,481

(22) Filed: Aug. 19, 2015

(65) Prior Publication Data

US 2016/0051637 A1 Feb. 25, 2016

Related U.S. Application Data

(60) Provisional application No. 62/039,362, filed on Aug. 19, 2014.

(51) Int. Cl.
*A61K 38/46* (2006.01)

(52) U.S. Cl.
CPC .... *A61K 38/465* (2013.01); *C12Y 301/01034* (2013.01)

(58) Field of Classification Search
CPC .................................................. A61K 38/465
USPC .................................. 435/198, 320.1, 252.3
See application file for complete search history.

(56) References Cited

U.S. PATENT DOCUMENTS 7,056,720 B2 * 6/2006 Jaye ........................ C12N 9/20
424/94.6

FOREIGN PATENT DOCUMENTS

| | | | |
|---|---|---|---|
| WO | WO-01/00220 | A2 | 1/2001 |
| WO | WO-03/039583 | A1 | 5/2003 |
| WO | WO-2005/123117 | A1 | 12/2005 |
| WO | WO-2010/054324 | A2 | 5/2010 |
| WO | WO-2010/134806 | A1 | 11/2010 |

OTHER PUBLICATIONS

International Search Report for PCT/US2015/045921, mailed Feb. 25, 2016.

Liu, J. et al., Angiopoietin-like Protein 3 Inhibits Lipoprotein Lipase Activity through Enhancing Its Cleavage by Proprotein Convertases, The Journal of Biological Chemistry, 285(36):27561-27570 (2010).

Yin, F. et al., A quantitative assay measuring the function of lipase maturation factor 1, Journal of Lipid Research, 50:2265-2269 (2009).

* cited by examiner

*Primary Examiner* — Maryam Monshipouri
(74) *Attorney, Agent, or Firm* — Fangli Chen; Proskauer Rose LLP

(57) ABSTRACT

A lipoprotein lipase (LPL) protein for treating and/or preventing HTG and its associated diseases, including but not limited to acute pancreatitis (AP), and in particular, acute pancreatitis secondary to or exacerbated by hypertriglyceridemia, and hypertriglyceridemia and its associated diseases in general, including cardiovascular and metabolic diseases, endocrine disorders, and fat embolism syndrome.

14 Claims, 4 Drawing Sheets

| | 5 minutes | | 20 minutes | |
|---|---|---|---|---|
| | N | serum TG, mg/dl | N | serum TG, mg/dl |
| VEHICLE | 10 | 315.6±90.7 | 10 | 194.6±64.8 |
| LPL, 1 mg/kg | 11 | 23.7±4.2 | 11 | 26.3±10.9 |

| | 5 minutes | | 20 minutes | |
|---|---|---|---|---|
| | N | serum TG, mg/dl | N | serum TG, mg/dl |
| VEHICLE | 7 | 236.6±85.4 | 7 | 239.7±87.8 |
| LPL, 0.1 mg/kg | 8 | 123.0±38.0 | 8 | 82.5±76.1 |
| LPL, 0.5 mg/kg | 8 | 49.5±30.0 | 8 | 51.3±29.3 |
| LPL, 1 mg/kg | 5 | 32.9±14.8 | 5 | 20.2±8.1 |

SEQUENCE LISTING

```
<160> NUMBER OF SEQ ID NOS: 7

<210> SEQ ID NO 1
<211> LENGTH: 448
<212> TYPE: PRT
<213> ORGANISM: Artificial Sequence
<220> FEATURE:
<223> OTHER INFORMATION: chemically synthesized polypeptide

<400> SEQUENCE: 1

Ala Asp Gln Arg Arg Asp Phe Ile Asp Ile Glu Ser Lys Phe Ala Leu
1               5                   10                  15

Arg Thr Pro Glu Asp Thr Ala Glu Asp Thr Cys His Leu Ile Pro Gly
            20                  25                  30

Val Ala Glu Ser Val Ala Thr Cys His Phe Asn His Ser Ser Lys Thr
        35                  40                  45

Phe Met Val Ile His Gly Trp Thr Val Thr Gly Met Tyr Glu Ser Trp
    50                  55                  60

Val Pro Lys Leu Val Ala Ala Leu Tyr Lys Arg Glu Pro Asp Ser Asn
65                  70                  75                  80

Val Ile Val Val Asp Trp Leu Ser Arg Ala Gln Glu His Tyr Pro Val
                85                  90                  95

Ser Ala Gly Tyr Thr Lys Leu Val Gly Gln Asp Val Ala Arg Phe Ile
            100                 105                 110

Asn Trp Met Glu Glu Glu Phe Asn Tyr Pro Leu Asp Asn Val His Leu
        115                 120                 125
```

```
Leu Gly Tyr Ser Leu Gly Ala His Ala Ala Gly Ile Ala Gly Ser Leu
    130                 135                 140

Thr Asn Lys Lys Val Asn Arg Ile Thr Gly Leu Asp Pro Ala Gly Pro
145                 150                 155                 160

Asn Phe Glu Tyr Ala Glu Ala Pro Ser Arg Leu Ser Pro Asp Asp Ala
                165                 170                 175

Asp Phe Val Asp Val Leu His Thr Phe Thr Arg Gly Ser Pro Gly Arg
            180                 185                 190

Ser Ile Gly Ile Gln Lys Pro Val Gly His Val Asp Ile Tyr Pro Asn
        195                 200                 205

Gly Gly Thr Phe Gln Pro Gly Cys Asn Ile Gly Glu Ala Ile Arg Val
    210                 215                 220

Ile Ala Glu Arg Gly Leu Gly Asp Val Asp Gln Leu Val Lys Cys Ser
225                 230                 235                 240

His Glu Arg Ser Ile His Leu Phe Ile Asp Ser Leu Leu Asn Glu Glu
                245                 250                 255

Asn Pro Ser Lys Ala Tyr Arg Cys Ser Ser Lys Glu Ala Phe Glu Lys
            260                 265                 270

Gly Leu Cys Leu Ser Cys Arg Lys Asn Arg Cys Asn Asn Leu Gly Tyr
        275                 280                 285

Glu Ile Asn Lys Val Arg Ala Lys Arg Ser Ser Lys Met Tyr Leu Lys
    290                 295                 300

Thr Arg Ser Gln Met Pro Tyr Lys Val Phe His Tyr Gln Val Lys Ile
305                 310                 315                 320

His Phe Ser Gly Thr Glu Ser Glu Thr His Thr Asn Gln Ala Phe Glu
                325                 330                 335

Ile Ser Leu Tyr Gly Thr Val Ala Glu Ser Glu Asn Ile Pro Phe Thr
            340                 345                 350

Leu Pro Glu Val Ser Thr Asn Lys Thr Tyr Ser Phe Leu Ile Tyr Thr
        355                 360                 365

Glu Val Asp Ile Gly Glu Leu Leu Met Leu Lys Leu Lys Trp Lys Ser
    370                 375                 380

Asp Ser Tyr Phe Ser Trp Ser Asp Trp Trp Ser Ser Pro Gly Phe Ala
385                 390                 395                 400

Ile Gln Lys Ile Arg Val Lys Ala Gly Glu Thr Gln Lys Lys Val Ile
                405                 410                 415

Phe Cys Ser Arg Glu Lys Val Ser His Leu Gln Lys Gly Lys Ala Pro
            420                 425                 430

Ala Val Phe Val Lys Cys His Asp Lys Ser Leu Asn Lys Lys Ser Gly
        435                 440                 445


<210> SEQ ID NO 2
<211> LENGTH: 448
<212> TYPE: PRT
<213> ORGANISM: Artificial Sequence
<220> FEATURE:
<223> OTHER INFORMATION: chemically syntehsized polypeptide

<400> SEQUENCE: 2

Ala Asp Gln Arg Arg Asp Phe Ile Asp Ile Glu Ser Lys Phe Ala Leu
1               5                   10                  15

Arg Thr Pro Glu Asp Thr Ala Glu Asp Thr Cys His Leu Ile Pro Gly
            20                  25                  30

Val Ala Glu Ser Val Ala Thr Cys His Phe Asn His Ser Ser Lys Thr
        35                  40                  45
```

```
Phe Met Val Ile His Gly Trp Thr Val Thr Gly Met Tyr Glu Ser Trp
    50                  55                  60

Val Pro Lys Leu Val Ala Ala Leu Tyr Lys Arg Glu Pro Asp Ser Asn
65                  70                  75                  80

Val Ile Val Val Asp Trp Leu Ser Arg Ala Gln Glu His Tyr Pro Val
                85                  90                  95

Ser Ala Gly Tyr Thr Lys Leu Val Gly Gln Asp Val Ala Arg Phe Ile
            100                 105                 110

Asn Trp Met Glu Glu Glu Phe Asn Tyr Pro Leu Asp Asn Val His Leu
        115                 120                 125

Leu Gly Tyr Ser Leu Gly Ala His Ala Ala Gly Ile Ala Gly Ser Leu
    130                 135                 140

Thr Asn Lys Lys Val Asn Arg Ile Thr Gly Leu Asp Pro Ala Gly Pro
145                 150                 155                 160

Asn Phe Glu Tyr Ala Glu Ala Pro Ser Arg Leu Ser Pro Asp Asp Ala
                165                 170                 175

Asp Phe Val Asp Val Leu His Thr Phe Thr Arg Gly Ser Pro Gly Arg
            180                 185                 190

Ser Ile Gly Ile Gln Lys Pro Val Gly His Val Asp Ile Tyr Pro Asn
        195                 200                 205

Gly Gly Thr Phe Gln Pro Gly Cys Asn Ile Gly Glu Ala Ile Arg Val
    210                 215                 220

Ile Ala Glu Arg Gly Leu Gly Asp Val Asp Gln Leu Val Lys Cys Ser
225                 230                 235                 240

His Glu Arg Ser Ile His Leu Phe Ile Asp Ser Leu Leu Asn Glu Glu
                245                 250                 255

Asn Pro Ser Lys Ala Tyr Arg Cys Ser Ser Lys Glu Ala Phe Glu Lys
            260                 265                 270

Gly Leu Cys Leu Ser Cys Arg Lys Asn Arg Cys Asn Asn Leu Gly Tyr
        275                 280                 285

Glu Ile Asn Lys Val Arg Ala Lys Ala Ser Ser Lys Met Tyr Leu Lys
    290                 295                 300

Thr Arg Ser Gln Met Pro Tyr Lys Val Phe His Tyr Gln Val Lys Ile
305                 310                 315                 320

His Phe Ser Gly Thr Glu Ser Glu Thr His Thr Asn Gln Ala Phe Glu
                325                 330                 335

Ile Ser Leu Tyr Gly Thr Val Ala Glu Ser Glu Asn Ile Pro Phe Thr
            340                 345                 350

Leu Pro Glu Val Ser Thr Asn Lys Thr Tyr Ser Phe Leu Ile Tyr Thr
        355                 360                 365

Glu Val Asp Ile Gly Glu Leu Leu Met Leu Lys Leu Lys Trp Lys Ser
    370                 375                 380

Asp Ser Tyr Phe Ser Trp Ser Asp Trp Trp Ser Ser Pro Gly Phe Ala
385                 390                 395                 400

Ile Gln Lys Ile Arg Val Lys Ala Gly Glu Thr Gln Lys Lys Val Ile
                405                 410                 415

Phe Cys Ser Arg Glu Lys Val Ser His Leu Gln Lys Gly Lys Ala Pro
            420                 425                 430

Ala Val Phe Val Lys Cys His Asp Lys Ser Leu Asn Lys Lys Ser Gly
        435                 440                 445

<210> SEQ ID NO 3
<211> LENGTH: 475
<212> TYPE: PRT
```

```
<213> ORGANISM: Artificial Sequence
<220> FEATURE:
<223> OTHER INFORMATION: chemically synthesized polypeptide

<400> SEQUENCE: 3

Met Glu Ser Lys Ala Leu Leu Val Leu Thr Leu Ala Val Trp Leu Gln
1               5                   10                  15

Ser Leu Thr Ala Ser Arg Gly Gly Val Ala Ala Ala Asp Gln Arg Arg
            20                  25                  30

Asp Phe Ile Asp Ile Glu Ser Lys Phe Ala Leu Arg Thr Pro Glu Asp
        35                  40                  45

Thr Ala Glu Asp Thr Cys His Leu Ile Pro Gly Val Ala Glu Ser Val
    50                  55                  60

Ala Thr Cys His Phe Asn His Ser Ser Lys Thr Phe Met Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
            100                 105                 110

Trp Leu Ser Arg Ala Gln Glu His Tyr Pro Val Ser Ala Gly Tyr Thr
        115                 120                 125

Lys Leu Val Gly Gln Asp Val Ala Arg Phe Ile Asn Trp Met Glu Glu
    130                 135                 140

Glu Phe Asn Tyr Pro Leu Asp Asn Val His Leu Leu Gly Tyr Ser Leu
145                 150                 155                 160

Gly Ala His Ala Ala Gly Ile Ala Gly Ser Leu Thr Asn Lys Lys Val
                165                 170                 175

Asn Arg Ile Thr Gly Leu Asp Pro Ala Gly Pro Asn Phe Glu Tyr Ala
            180                 185                 190

Glu Ala Pro Ser Arg Leu Ser Pro Asp Asp Ala Asp Phe Val Asp Val
        195                 200                 205

Leu His Thr Phe Thr Arg Gly Ser Pro Gly Arg Ser Ile Gly Ile Gln
    210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
                245                 250                 255

Leu Gly Asp Val Asp Gln Leu Val Lys Cys Ser His Glu Arg Ser Ile
            260                 265                 270

His Leu Phe Ile Asp Ser Leu Leu Asn Glu Glu Asn Pro Ser Lys Ala
        275                 280                 285

Tyr Arg Cys Ser Ser Lys Glu Ala Phe Glu Lys Gly Leu Cys Leu Ser
    290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
                325                 330                 335

Pro Tyr Lys Val Phe His Tyr Gln Val Lys Ile His Phe Ser Gly Thr
            340                 345                 350

Glu Ser Glu Thr His Thr Asn Gln Ala Phe Glu Ile Ser Leu Tyr Gly
        355                 360                 365

Thr Val Ala Glu Ser Glu Asn Ile Pro Phe Thr Leu Pro Glu Val Ser
    370                 375                 380

Thr Asn Lys Thr Tyr Ser Phe Leu Ile Tyr Thr Glu Val Asp Ile Gly
```

```
385                 390                 395                 400

Glu Leu Leu Met Leu Lys Leu Lys Trp Lys Ser Asp Ser Tyr Phe Ser
                405                 410                 415

Trp Ser Asp Trp Trp Ser Ser Pro Gly Phe Ala Ile Gln Lys Ile Arg
            420                 425                 430

Val Lys Ala Gly Glu Thr Gln Lys Lys Val Ile Phe Cys Ser Arg Glu
        435                 440                 445

Lys Val Ser His Leu Gln Lys Gly Lys Ala Pro Ala Val Phe Val Lys
    450                 455                 460

Cys His Asp Lys Ser Leu Asn Lys Lys Ser Gly
465                 470                 475


<210> SEQ ID NO 4
<211> LENGTH: 312
<212> TYPE: PRT
<213> ORGANISM: Artificial Sequence
<220> FEATURE:
<223> OTHER INFORMATION: chemically synthesized polypeptide

<400> SEQUENCE: 4

Ala Asp Gln Arg Arg Asp Phe Ile Asp Ile Glu Ser Lys Phe Ala Leu
1               5                   10                  15

Arg Thr Pro Glu Asp Thr Ala Glu Asp Thr Cys His Leu Ile Pro Gly
            20                  25                  30

Val Ala Glu Ser Val Ala Thr Cys His Phe Asn His Ser Ser Lys Thr
        35                  40                  45

Phe Met Val Ile His Gly Trp Thr Val Thr Gly Met Tyr Glu Ser Trp
    50                  55                  60

Val Pro Lys Leu Val Ala Ala Leu Tyr Lys Arg Glu Pro Asp Ser Asn
65                  70                  75                  80

Val Ile Val Val Asp Trp Leu Ser Arg Ala Gln Glu His Tyr Pro Val
                85                  90                  95

Ser Ala Gly Tyr Thr Lys Leu Val Gly Gln Asp Val Ala Arg Phe Ile
            100                 105                 110

Asn Trp Met Glu Glu Glu Phe Asn Tyr Pro Leu Asp Asn Val His Leu
        115                 120                 125

Leu Gly Tyr Ser Leu Gly Ala His Ala Ala Gly Ile Ala Gly Ser Leu
    130                 135                 140

Thr Asn Lys Lys Val Asn Arg Ile Thr Gly Leu Asp Pro Ala Gly Pro
145                 150                 155                 160

Asn Phe Glu Tyr Ala Glu Ala Pro Ser Arg Leu Ser Pro Asp Asp Ala
                165                 170                 175

Asp Phe Val Asp Val Leu His Thr Phe Thr Arg Gly Ser Pro Gly Arg
            180                 185                 190

Ser Ile Gly Ile Gln Lys Pro Val Gly His Val Asp Ile Tyr Pro Asn
        195                 200                 205

Gly Gly Thr Phe Gln Pro Gly Cys Asn Ile Gly Glu Ala Ile Arg Val
    210                 215                 220

Ile Ala Glu Arg Gly Leu Gly Asp Val Asp Gln Leu Val Lys Cys Ser
225                 230                 235                 240

His Glu Arg Ser Ile His Leu Phe Ile Asp Ser Leu Leu Asn Glu Glu
                245                 250                 255

Asn Pro Ser Lys Ala Tyr Arg Cys Ser Ser Lys Glu Ala Phe Glu Lys
            260                 265                 270

Gly Leu Cys Leu Ser Cys Arg Lys Asn Arg Cys Asn Asn Leu Gly Tyr
```

```
        275                 280                 285

Glu Ile Asn Lys Val Arg Ala Lys Arg Ser Ser Lys Met Tyr Leu Lys
    290                 295                 300

Thr Arg Ser Gln Met Pro Tyr Lys
305                 310


<210> SEQ ID NO 5
<211> LENGTH: 136
<212> TYPE: PRT
<213> ORGANISM: Artificial Sequence
<220> FEATURE:
<223> OTHER INFORMATION: chemically synthesized polypeptide

<400> SEQUENCE: 5

Val Phe His Tyr Gln Val Lys Ile His Phe Ser Gly Thr Glu Ser Glu
1               5                   10                  15

Thr His Thr Asn Gln Ala Phe Glu Ile Ser Leu Tyr Gly Thr Val Ala
            20                  25                  30

Glu Ser Glu Asn Ile Pro Phe Thr Leu Pro Glu Val Ser Thr Asn Lys
        35                  40                  45

Thr Tyr Ser Phe Leu Ile Tyr Thr Glu Val Asp Ile Gly Glu Leu Leu
    50                  55                  60

Met Leu Lys Leu Lys Trp Lys Ser Asp Ser Tyr Phe Ser Trp Ser Asp
65                  70                  75                  80

Trp Trp Ser Ser Pro Gly Phe Ala Ile Gln Lys Ile Arg Val Lys Ala
                85                  90                  95

Gly Glu Thr Gln Lys Lys Val Ile Phe Cys Ser Arg Glu Lys Val Ser
            100                 105                 110

His Leu Gln Lys Gly Lys Ala Pro Ala Val Phe Val Lys Cys His Asp
        115                 120                 125

Lys Ser Leu Asn Lys Lys Ser Gly
    130                 135


<210> SEQ ID NO 6
<211> LENGTH: 446
<212> TYPE: PRT
<213> ORGANISM: Artificial Sequence
<220> FEATURE:
<223> OTHER INFORMATION: chemically synthesized polypeptide

<400> SEQUENCE: 6

Ala Asp Gln Arg Arg Asp Phe Ile Asp Ile Glu Ser Lys Phe Ala Leu
1               5                   10                  15

Arg Thr Pro Glu Asp Thr Ala Glu Asp Thr Cys His Leu Ile Pro Gly
            20                  25                  30

Val Ala Glu Ser Val Ala Thr Cys His Phe Asn His Ser Ser Lys Thr
        35                  40                  45

Phe Met Val Ile His Gly Trp Thr Val Thr Gly Met Tyr Glu Ser Trp
    50                  55                  60

Val Pro Lys Leu Val Ala Ala Leu Tyr Lys Arg Glu Pro Asp Ser Asn
65                  70                  75                  80

Val Ile Val Val Asp Trp Leu Ser Arg Ala Gln Glu His Tyr Pro Val
                85                  90                  95

Ser Ala Gly Tyr Thr Lys Leu Val Gly Gln Asp Val Ala Arg Phe Ile
            100                 105                 110

Asn Trp Met Glu Glu Glu Phe Asn Tyr Pro Leu Asp Asn Val His Leu
        115                 120                 125
```

```
Leu Gly Tyr Ser Leu Gly Ala His Ala Ala Gly Ile Ala Gly Ser Leu
    130                 135                 140

Thr Asn Lys Lys Val Asn Arg Ile Thr Gly Leu Asp Pro Ala Gly Pro
145                 150                 155                 160

Asn Phe Glu Tyr Ala Glu Ala Pro Ser Arg Leu Ser Pro Asp Asp Ala
                165                 170                 175

Asp Phe Val Asp Val Leu His Thr Phe Thr Arg Gly Ser Pro Gly Arg
            180                 185                 190

Ser Ile Gly Ile Gln Lys Pro Val Gly His Val Asp Ile Tyr Pro Asn
        195                 200                 205

Gly Gly Thr Phe Gln Pro Gly Cys Asn Ile Gly Glu Ala Ile Arg Val
    210                 215                 220

Ile Ala Glu Arg Gly Leu Gly Asp Val Asp Gln Leu Val Lys Cys Ser
225                 230                 235                 240

His Glu Arg Ser Ile His Leu Phe Ile Asp Ser Leu Leu Asn Glu Glu
                245                 250                 255

Asn Pro Ser Lys Ala Tyr Arg Cys Ser Ser Lys Glu Ala Phe Glu Lys
            260                 265                 270

Gly Leu Cys Leu Ser Cys Arg Lys Asn Arg Cys Asn Asn Leu Gly Tyr
        275                 280                 285

Glu Ile Asn Lys Val Arg Ala Lys Arg Ser Ser Lys Met Tyr Leu Lys
    290                 295                 300

Thr Arg Ser Gln Met Pro Tyr Lys Val Phe His Tyr Gln Val Lys Ile
305                 310                 315                 320

His Phe Ser Gly Thr Glu Ser Glu Thr His Thr Asn Gln Ala Phe Glu
                325                 330                 335

Ile Ser Leu Tyr Gly Thr Val Ala Glu Ser Glu Asn Ile Pro Phe Thr
            340                 345                 350

Leu Pro Glu Val Ser Thr Asn Lys Thr Tyr Ser Phe Leu Ile Tyr Thr
        355                 360                 365

Glu Val Asp Ile Gly Glu Leu Leu Met Leu Lys Leu Lys Trp Lys Ser
    370                 375                 380

Asp Ser Tyr Phe Ser Trp Ser Asp Trp Trp Ser Ser Pro Gly Phe Ala
385                 390                 395                 400

Ile Gln Lys Ile Arg Val Lys Ala Gly Glu Thr Gln Lys Lys Val Ile
                405                 410                 415

Phe Cys Ser Arg Glu Lys Val Ser His Leu Gln Lys Gly Lys Ala Pro
            420                 425                 430

Ala Val Phe Val Lys Cys His Asp Lys Ser Leu Asn Lys Lys
        435                 440                 445


<210> SEQ ID NO 7
<211> LENGTH: 10
<212> TYPE: PRT
<213> ORGANISM: Artificial Sequence
<220> FEATURE:
<223> OTHER INFORMATION: chemically synthesized polypeptide

<400> SEQUENCE: 7

Glu Gln Lys Leu Ile Ser Glu Glu Asp Leu
1               5                   10
```

LIPOPROTEIN LIPASE FOR TREATMENT OF HYPERTRIGLYCERIDEMIC-RELATED CONDITIONS INCLUDING ACUTE PANCREATITIS

CROSS REFERENCE TO RELATED APPLICATIONS

This application claims priority to U.S. Provisional Application 62/039,362 filed Aug. 19, 2014, which is incorporated by reference in its entirety.

SEQUENCE LISTING

The instant application contains a Sequence Listing which has been submitted electronically in ASCII format and is hereby incorporated by reference in its entirety. Said ASCII copy, created on Oct. 8$^{th}$, 2015, is named "2006685-1206_ST25", and is 20,614 bytes in size.

TECHNICAL FIELD

This invention relates to compositions, uses, and methods for treating and/or preventing conditions associated with elevated triglyceride levels, such as hypertriglyceridemia (HTG) and its associated diseases, including but not limited to acute pancreatitis (AP) (in particular, acute pancreatitis secondary to or exacerbated by hypertriglyceridemia), cardiovascular and metabolic diseases, endocrine disorders such as hypothyroidism, and fat embolism syndrome.

BACKGROUND

Hypertriglyceridemia

Hypertriglyceridemia (HTG) is a condition in which triglyceride (TG) levels are elevated in the blood. The National Cholesterol Education Program Adult Treatment Panel (NCEP ATP III) guidelines indicate that normal TG levels are <150 mg/dl. HTG can be classified into primary or secondary types. Primary HTG is caused by genetic defects resulting in abnormal triglyceride metabolism. Secondary HTG is the result of acquired causes such as diabetes, obesity, hypothyroidism, and certain medications. HTG is frequently associated with other lipid abnormalities and metabolic syndrome, and is a risk factor for atherosclerosis and cardiovascular disease.

Hypertriglyceridemia-Induced Acute Pancreatitis

HTG is a rare but significant cause of AP. Hypertriglyceridemic acute pancreatitis (HTGAP) accounts for approximately 1-11% of all cases of AP. These numbers may represent somewhat of an underestimation; some investigators have suggested that HTGAP is under diagnosed, as not all patients diagnosed with AP have TG levels checked upon their initial presentation to the hospital, and some patients with severe HTG and abdominal pain are not correctly diagnosed with pancreatitis. Additionally, it has been suggested that moderately elevated levels of TG may exacerbate AP associated with other causative factors.

The mechanism by which HTG causes AP is currently being investigated. Without wishing to be bound by theory, one hypothesis suggests that hydrolysis of excess TGs by pancreatic lipases leads to the liberation of large amounts of free fatty acids (FFA) within the pancreas, which initiates the process of pancreatic injury, and pancreatic enzyme activation and release. Another hypothesis suggests that the pathologic process is initiated by poor pancreatic perfusion due to hyperviscosity of the hyperlipidemic blood, which leads to ischemia, hydrolysis of TG by pancreatic lipase, and a continuous cycle of pancreatic injury. Genetic studies in animal models also support a mechanistic link between HTG and AP. For example, it has been found that LPL-deficient minks developed spontaneous pancreatitis. LPL-deficient mice showed an enhanced susceptibility to pancreatitis. Furthermore, high plasma TG has been shown to exacerbate AP in rats.

While a value at which patients with elevated TGs develop AP is not precisely defined, the risk of developing HTGAP increases significantly when TG levels are above 1000 mg/dl.

AP is an inflammatory disease of the pancreas. Patients typically present with acute upper abdominal pain, nausea and vomiting. The diagnosis is based on patient symptoms, specifically type and location of abdominal pain, laboratory tests, including serum amylase and lipase levels, and radiologic evaluations, including ultrasound, Computed Tomography (CT) or Magnetic Resonance Imaging (MRI).

AP leads to the release and activation of digestive enzymes, such as trypsinogen, from the exocrine pancreas gland causing inflammation, injury, and autolysis of the pancreas. AP is a disease with significant morbidity and mortality. Patients with AP may develop multi-organ failure, pancreatic necrosis, pancreatic pseudocysts, infection, and shock. Prolonged ICU stays are common, and various invasive procedures may be required. The overall mortality rate for all levels of severity is approximately 5%, however for the sickest patients, those with infected pancreatic necrosis, mortality has been reported to be as high as 62%. Long term consequences of AP include glucose intolerance, pancreatic insufficiency, and recurrent pancreatitis.

Gallstones and alcohol abuse are by far the two most common causes of AP, with multiple less frequently occurring etiologies, including hypertriglyceridemia, undergoing ERCP, drugs, hereditary AP, among others.

Pancreatitis can be categorized into different categories based on level of pancreatic injury, and clinical presentation. Based on radiologic examinations, AP can be described as either interstitial edematous pancreatitis, or necrotizing pancreatitis, with necrotizing pancreatitis being the more severe. In addition, AP can be described as mild, moderate, or severe, using the revised Atlanta Criteria, which defines categories based on the patient's clinical condition, such as the presence or absence of organ failure: e.g., no organ failure=mild, transient organ failure (<48 hours)=moderate, and persistent organ failure=severe. Patients can also be evaluated for severity of illness based on a large variety of clinical assessment tools (e.g., APACHE II, Balthazar criteria, SIRS criteria etc.).

No specific pharmacological interventions have been demonstrated to improve the clinical course of AP. Current treatment is limited to supportive therapy: IV hydration, pain control, nutritional support, intensive care; antibiotics and surgical interventions are implemented as needed. While approximately 80% of cases may resolve with supportive therapy, with hospital stays typically lasting 5-7 days, 20% of patients have severe disease, which frequently require prolonged ICU stays, and may require invasive procedures. The mortality rate for all patients with AP is approximately 5%, while for the sickest patients the mortality rate has been reported to be upwards of 60%. In patients with HTGAP, one exemplary goal of therapy is to lower TG levels as quickly as possible, in an attempt to intervene in the process of continued pancreatic injury. Currently this can be achieved through aggressive hydration and nutritional management.

With supportive care, TG levels have been reported to decrease to ≤500 mg/dl by 72 hours in most but not all patients. Various therapeutic interventions to quickly reduce TG levels have been attempted, however there are currently no approaches that have proven to be reproducibly effective and safe.

It has been suggested that HTGAP may be a more aggressive form of pancreatitis. Due to the small number of patients accurately diagnosed with HTGAP, there have been few studies large enough to adequately address this issue. Two studies that examined larger numbers of patients with HTGAP found that compared to patients with biliary pancreatitis, patients with HTGAP tend to be younger, and more likely to progress to severe disease.

Fat Embolism

Fat embolism syndrome is a potentially fatal complication of trauma to fat-containing bones and soft tissue and is characterized by deposits of fat globules in the circulation. Fat embolism syndrome is more likely to develop after lower limb and pelvic fractures in contrast to fractures of upper limbs. The primary symptoms and signs of fat embolism syndrome are respiratory distress, neurological signs including confusion, drowsiness, convulsions, coma, and petechial rash. Fat embolism can lead to severe complications such as pulmonary dysfunction and microinfarctions. Treatment is limited to supportive care, and focuses primarily on minimizing pulmonary distress and hypovolemia. The invention aims to provide improved methods of preventing and/or treating HTG and its associated diseases, including AP, cardiovascular disease, metabolic disorders, endocrine disorders, and fat embolism syndrome.

SUMMARY

The present invention provides, among other things, lipoprotein lipase (LPL) polypeptides, related compositions, and their use in treatment or prevention of various diseases, disorders, or conditions described herein. In some cases, the LPL polypeptides may be for use in the treatment or prevention of a hyperlipidemia and hyperlipidemia-related conditions, including hypertriglyceridemia (HTG) and hypertriglyceridemia-related conditions, in a subject. In some cases, the LPL polypeptide is substantially resistant to proteolytic cleavage by proprotein convertase. Methods for the treatment and/or prevention of hyperlipidemia and hyperlipidemia-related conditions (e.g., hypertriglyceridemia-related conditions) are also provided. The method may involve administering any of the LPL polypeptides disclosed herein to a subject.

In some cases, the hypertriglyceridemia-related condition is secondary to or exacerbated by hypertriglyceridemia. The hypertriglyceridemia-related condition may be, for example, hypertriglyceridemia, acute pancreatitis, cardiovascular disease, a metabolic disorder, an endocrine disorder, or fat embolism syndrome. In some embodiments, the hypertriglyceridemia-related condition is acute pancreatitis. In some embodiments, the acute pancreatitis is secondary to or exacerbated by hypertriglyceridemia. In some embodiments, the serum or plasma triglyceride level in the subject exceeds about 150 mg/dl.

In any of the foregoing embodiments, the LPL polypeptide may comprise or consist of an amino acid sequence having 80%, 90%, 95%, 99%, 99.5% or 99.8% or more identity to SEQ ID NO: 1. In some embodiments, the LPL polypeptide comprises or consists of the amino acid sequence of SEQ ID NO: 2. In some embodiments, the LPL polypeptide exhibits a $V_{max}$ of about 0.01-50 mmoles FA/hr/mg in a [$^3$H]-triolein liposome activity assay and/or a $K_m$ value of about 0.01-1 μM.

In any of the foregoing embodiments, the LPL polypeptide may be administered by oral, intravenous, intramuscular, intravenous, intranasal, intradermal, subcutaneous, or suppository route. In any of the foregoing embodiments, the LPL polypeptide may be administered by continuous infusion or by bolus injection. In any of the foregoing embodiments, the LPL polypeptide may be administered as a single dose or multiple doses.

In any of the foregoing embodiments, the LPL polypeptide may be glycosylated. In any of the foregoing embodiments, the LPL polypeptide may be non-glycosylated.

In some cases, the LPL polypeptide is in aqueous form. In some cases, the LPL polypeptide is in lyophilized form.

Methods of preparing the LPL polypeptide disclosed herein are also provided. In some embodiments, the method may involve reconstituting an LPL polypeptide in lyophilized form with aqueous material. In some embodiments, the method may comprise performing recombinant expression of an LPL polypeptide and LMF1 in a cell. The cell may be a mammalian cell, a plant cell, an insect cell, or another type of cell. In some cases, the cell is a HT1080 cell, HEK293 cell, CHO cell, or a variant of a CHO cell.

Pharmaceutical compositions are also provided. The pharmaceutical composition may comprise any of the LPL polypeptides disclosed herein, and a pharmaceutically acceptable carrier.

Methods of treating or preventing a hypertriglyceridemia-related condition in a subject are also provided comprising the step of administering to the subject an effective amount of an LPL polypeptide as disclosed herein or a pharmaceutical composition as disclosed herein.

Use of LPL polypeptides disclosed herein, or pharmaceutical compositions disclosed herein, in the preparation of a medicament for the treatment or prevention of a hypertriglyceridemia-related condition in a subject are also provided.

DISCLOSURE OF THE INVENTION

Figure 1:
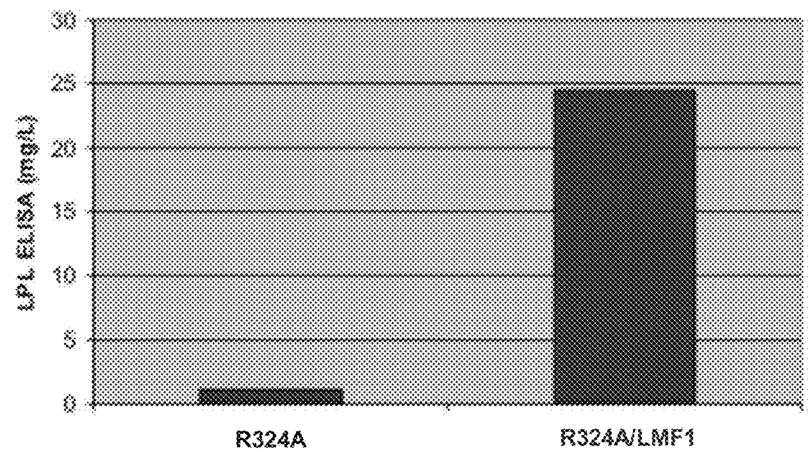
FIG. 1 shows LPL titer estimates of LPL expressed in HT1080 cells ("R324A") and in HT1080 cells co-transfected with LMF1 ("R324A/LMF1") by ELISA.

The invention provides a lipoprotein lipase (LPL) polypeptide for use in the treatment and/or prevention of HTG and its associated diseases, including but not limited to AP, cardiovascular disease, metabolic disorders, endocrine disorders, and fat embolism syndrome in a subject. The subject may have HTG. The serum triglyceride level in the subject may exceed approximately 150 mg/dl. The AP may be secondary to or exacerbated by hyperlipidemia, preferably HTG.

LPL can play a major role in the metabolism and transport of lipids as the enzyme responsible for the hydrolysis of triglycerides in chylomicrons and very low-density lipoproteins (VLDLs). LPL is primarily anchored to the luminal surface of capillary endothelial cells and can interact with lipoproteins and facilitate lipoprotein particle uptake. LPL can also promote the exchange of lipids between lipoproteins, and consequently has an important role in the kinetics of many lipoprotein particles. Thus, when used with the invention, LPL is capable of reducing plasma/serum triglyceride (TG) level in the subject, thereby ameliorating the symptoms of the diseases.

The invention uses LPL polypeptides, which include both wild-type LPL and its sequence variants. The invention preferably uses a human LPL polypeptide, e.g. the LPL polypeptide comprises or consists of the amino acid sequence recited in SEQ ID NO: 1. A LPL polypeptide used with the invention preferably comprises or consists of an amino acid sequence having 80%, 90%, 95%, 99%, 99.5% or 99.8% or more identity to a LPL polypeptide, e.g. the mature human lipoprotein lipase (LPL) (SEQ ID NO: 1). LPL polypeptides may exhibit certain properties (e.g., enzymatic properties), including a $V_{max}$ of about 0.01-50 mmoles/h/mg in a [$^3$H]-triolein liposome activity assay and/or a $K_m$ value of about 0.01-1 μM. In some cases, the LPL polypeptide may be substantially resistant to proteolytic cleavage, for example, by proprotein convertase (PC). For example, the LPL polypeptide may be a variant of LPL containing at least one point mutation that replaces, modifies or deletes any of the amino acids at the RAKR sequence located at amino acid positions 294-297 of SEQ ID NO: 1 (which corresponds to the amino acid positions 320-324 of the wild-type LPL precursor, SEQ ID NO: 3). In some cases, the LPL polypeptide may have an amino acid substitution at position 297 of SEQ ID NO: 1. Preferably, the LPL variant comprises or consists of the amino acid sequence recited in SEQ ID NO: 2 (referred to as LPL R324A herein). In some cases, the LPL polypeptide is not an S447X mutant of LPL (SEQ ID NO: 6).

The LPL polypeptide may be, for example, 448 amino acids in length, e.g. having the amino acid sequence of SEQ ID NO: 1 or 2. In other instances, the LPL polypeptide may be 446 amino acids in length, e.g. having the amino acid sequence of SEQ ID NO: 6.

In vivo, endogenous LPL is secreted as head-to-tail homodimers following synthesis. The LPL homodimers are translocated from the interstitial space to endothelial cells.

The LPL homodimers are anchored to endothelial cells by ion interaction with heparin sulfate proteoglycans (HSPG) and/or by glycosyl phosphatidylinositol (e.g. GPI-HBP1). LPL homodimers are active in the capillary lumen, and the activity requires interaction with the cofactor ApoCII. The inventors report herein that in plasma samples obtained from HTG patients with and without AP, when LPL polypeptide was added to the samples, LPL was capable of rapidly hydrolyzing TGs. This demonstrates that exogenously added LPL polypeptide remains enzymatically active in plasma, and is functional to reduce TG levels in a disease context.

Figure 3A:
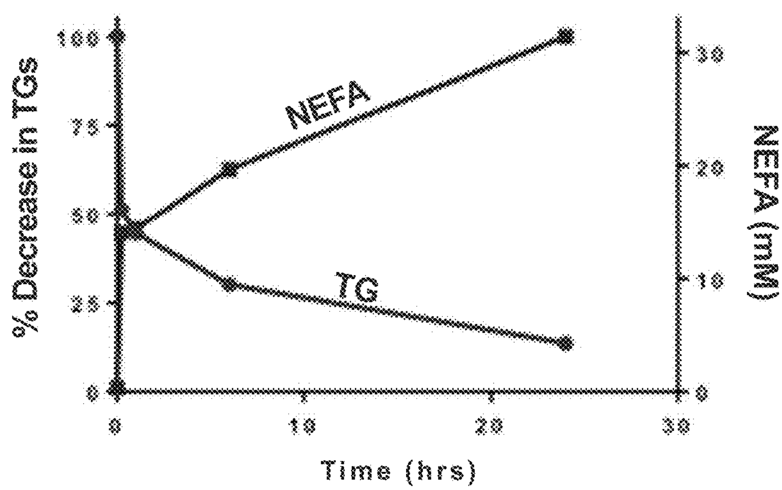
FIGS. 3A and 3B show representative time-courses in triglyceride (TG) and free fatty acid (FFA) concentrations in plasma samples from patients who have HTG (FIG. 3A) and HTGAP (FIG. 3B) following treatment with LPL. Baseline TG levels are 1250 mg/dl and 6202 mg/dl in FIGS. 3A and 3B respectively.
Figure 3B:
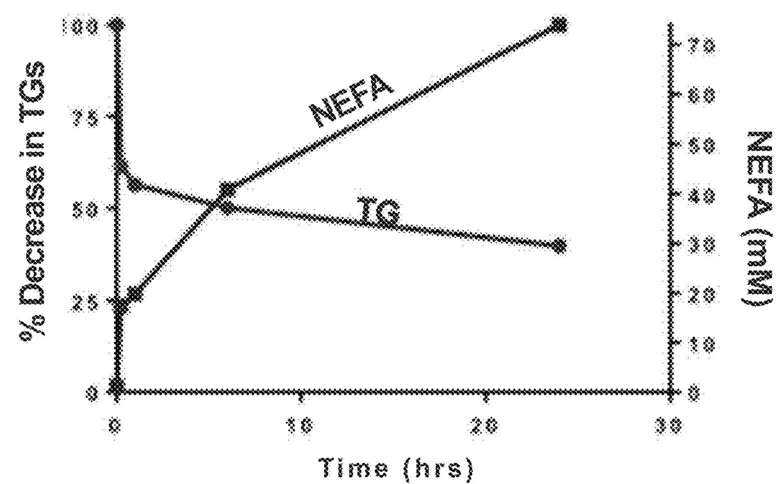
Figure 4A:
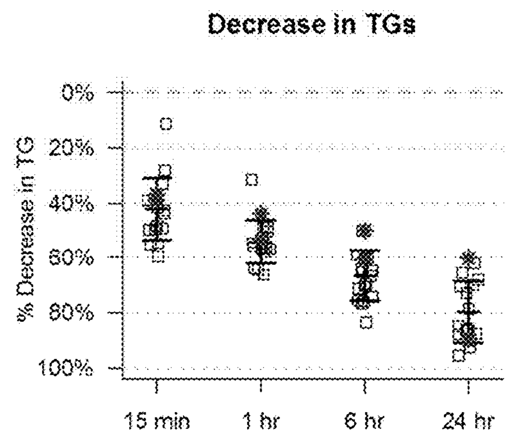
FIGS. 4A and 4B show changes in TG and FFA levels in plasma obtained in 16 HTG individuals (denoted by open squares) and 2 individuals with HTGAP (denoted by asterisk).
Figure 4B:
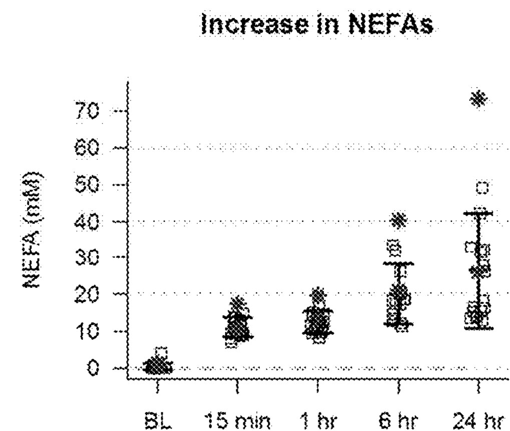
Figure 5:
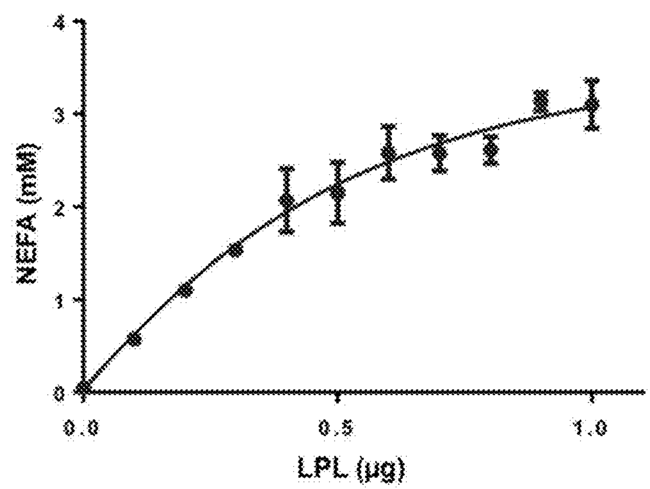
FIG. 5 shows the change in FFA concentration following incubation of increasing amounts of LPL in human HTG plasma demonstrating a dose-dependent hydrolysis of TGs.

In fact, LPL polypeptide is capable of rapidly hydrolyzing triglycerides in human plasma of HTG individuals and HTG individuals undergoing an attack of AP. This was demonstrated by incubating an isolated LPL polypeptide variant R324A in plasma samples obtained from 16 HTG individuals (baseline TG levels=1182±873 mg/dL, range 342-3449 mg/dL) and two individuals with HTGAP (baseline TG levels=1255 and 6202 mg/dL) for up to 24 hours and assessing changes in TG and non-esterified fatty acid or free fatty acid (FFA) levels. FIGS. 3A and 3B show representative time-courses of TG and FFA concentrations following incubation of LPL for an individual with HTG and HTGAP respectively (baseline TG levels=1250 mg/dl and 6202 mg/dl respectively). In both samples, LPL led to a rapid and precipitous decline of TGs along with a concomitant increase in FFAs (FIG. 3). This was observed across all HTG samples (FIG. 4, asterisk denotes HTGAP samples). Specifically, plasma TG levels decreased 42±11%, 54±8%, 67±9% and 79±11% at 15 minutes, 1 hour, 6 hours and 24 hours respectively across all HTG samples (all $p<0.001$) (FIG. 4A). Additionally a corresponding increase in FFAs consistent with the reduction in TG levels was observed in each of the samples (FIG. 4B). Treatment with LPL also resulted in a dose-dependent hydrolysis of TGs in HTG plasma as demonstrated by the increased release of FFAs following incubation with increasing amounts of LPL (FIG. 5).

Figures 6, 7, 8:
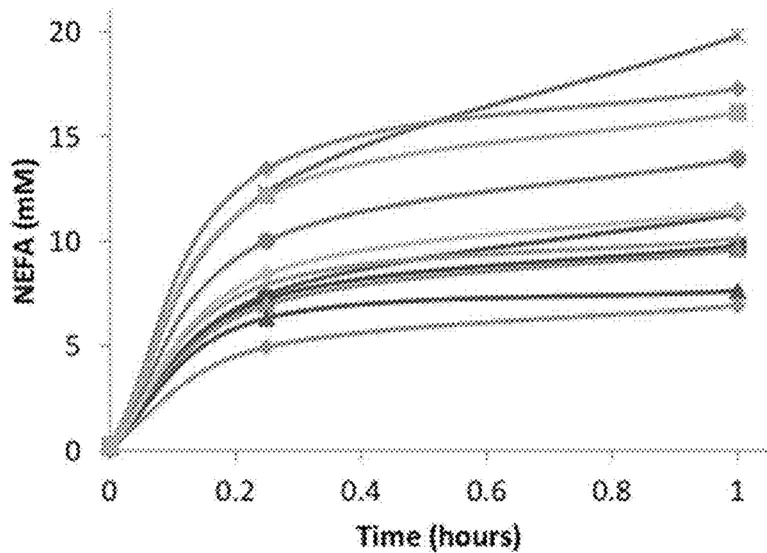
FIG. 6 shows changes in NEFA concentration in plasma obtained from 11 HTG NHPs following incubation with LPL (1 μg LPL in 125 μL plasma). Baseline plasma TGs were 1566±352 mg/dL (range=352-5360 mg/dL).
FIG. 7 shows serum TG levels following a single IV administration of recombinant LPL (1 mg/kg) or vehicle to ob/ob mice at 5 and 20 minutes post-injection. Data shown as mean±standard deviation.
FIG. 8 shows serum TG levels in ob/ob mice following a single IV administration of recombinant LPL at 0 (vehicle control), 0.1 mg/kg, 0.5 mg/kg and 1 mg/kg. Data shown as mean±standard deviation.

Embodiments disclosed herein provide for the use of LPL polypeptides in various therapeutic applications. Given that LPL had previously been known to have a very short half-life in humans (only 6-30 min), it was surprising that exogenous LPL exhibited sufficient activity in plasma to reduce TG levels in vivo, in a therapeutically-relevant way. Building upon the ex vivo experiments described herein, the inventors conducted various experiments in vivo, using the ob/ob mouse model. In these experiments, LPL R324A was administered intravenously (IV) at doses of 0.1 mg/kg, 0.5 mg/kg and 1 mg/kg. FIG. 7 shows a >85% drop in serum TG levels following a single IV administration of 1 mg/kg of recombinant LPL in ob/ob mice compared to vehicle controls ($p<0.001$). Despite the large drop in serum TGs, serum NEFA concentration remained unchanged. Fatty acids are rapidly transported to target tissues by albumin and thus our findings are consistent with the rapid clearance of fatty acids as reported in the literature. Furthermore, LPL elicited a dose-dependent hydrolysis of TGs consistent with ex vivo experiments (FIG. 8). This provides further evidence that an exogenously added LPL polypeptide has in vivo functional activity when administered.

Before commencing this work, an uncertainty faced the inventors, in that the AP condition causes the release of proteolytic enzymes from the gut into the plasma. The work reported herein is the first to show that LPL remains active in the presence of these proteolytic enzymes, to the extent that a real reduction in TG levels can be generated in a therapeutic context. This therefore paves the way for the observation that LPL and variants thereof could be effective in lowering TG levels, e.g. by hydrolyzing triglycerides in lipoproteins, such as those found in chylomicrons and very low-density lipoproteins (VLDL), in AP patients.

The LPL polypeptides used with the invention may be administered by oral, intravenous, intramuscular, intravenous, intranasal, intradermal, subcutaneous, or suppository routes. The LPL polypeptides of the invention may also be administered parenterally or intraperitoneally. In some cases, the LPL polypeptides may be administered to a subject via intravenous, subcutaneous or intra muscular injection, by continuous infusion, or by bolus injection. The LPL polypeptides used with the invention may be administered as a single dose or multiple doses.

The LPL polypeptides used with the invention are preferably glycosylated. A glycosylated polypeptide used in accordance with the invention preferably has a molecular weight of about 50-60 kDa. In some cases, the LPL polypeptides may be non-glycosylated, as some, or all of the N-linked consensus sites.

The LPL polypeptide preferably has a $V_{max}$ of about 0.01-50 mmoles/h/mg in a [$^3$H]-triolein liposome activity assay. Preferably, the LPL polypeptide of the invention has a $K_m$ value of about 0.01-1 μM.

LPL is preferably administered in the form of protein into a subject. The LPL polypeptide used with the invention may be in aqueous form or a formulation compatible with the hydrophobic nature of the molecule, including but not limited to lipid or polymeric nanoparticles.

The invention may use a lyophilizate of the LPL polypeptides of the invention. This lyophilizate can be reconstituted with aqueous material to provide an aqueous composition comprising the LPL polypeptide of the invention. For administration, the lyophilizate is thus reconstituted with a suitable liquid diluent (e.g. a buffer, saline solution, water for injection (wfi)).

The invention also provides a pharmaceutical composition comprising a LPL polypeptide of the invention (e.g., wild-type LPL or a variant thereof) and a pharmaceutically acceptable carrier.

The invention also provides a method of preparing a LPL polypeptide of the invention, comprising performing the recombinant expression of the LPL polypeptide together with the LMF1 protein in a cell. Suitable expression systems may be stable or transient expression systems. The cell may be a mammalian cell, a plant cell, an insect cell, or other types of cells. Preferably, the cell is a HT1080, HEK293, COS or CHO cell (including all CHO variants).

The invention preferably uses LPL polypeptides in enzyme therapy, i.e. the LPL is administered in the form of protein. This is in contrast to a gene therapy, which involves administering the subject with a viral nucleic acid encoding a protein such as LPL. LPL enzyme therapy provides the subject with a supply of LPL polypeptides, and this sudden increase in LPL polypeptide concentration is capable of allowing a rapid reduction in plasma/serum TG level and/or maintaining plasma/serum TG at a certain concentration to prevent conditions related to HTG.

LPL and Variants

The lipoprotein lipase protein is herein annotated as 'LPL' (EC 3.1.1.34). LPL was originally called 'heparin-releasable clearing factor', and has also been referred to as 'clearing factor lipase', 'diacylglycerol lipase', 'diglyceride lipase', 'HDLCQ11' and 'LIPD' in the literature.

In humans, a wild-type LPL has the amino acid sequence SEQ ID NO: 3 (NP_000228, GI: 4557727). LPL is initially translated as a precursor protein, having 475 amino acids (SEQ ID NO: 3). In action, the signal peptide at amino acid positions 1-27 of SEQ ID NO: 3 is then cleaved, leaving the mature form having roughly 448 amino acids (e.g. SEQ ID NO: 1).

The invention preferably uses a human LPL polypeptide, e.g. the LPL polypeptide comprises or consists of the amino acid sequence recited in SEQ ID NO: 1 or 3. Preferably, the LPL polypeptide comprises or consists of the amino acid sequence recited in SEQ ID NO: 1.

A LPL polypeptide used in accordance with the invention may comprise or consist of an amino acid sequence having 80% or more identity (e.g. 85%, 90%, 91%, 92%, 93%, 94%, 95%, 96%, 97%, 98%, 99%, 99.5%, 99.8% or more) to wild-type LPL, e.g., the LPL polypeptide used with the invention may comprise or consist of any of the amino acid sequences recited in SEQ ID NOs: 1-6.

Preferably, a LPL polypeptide used with the invention may retain the activity of the wild-type LPL. For example, the LPL polypeptide may exhibit activity that is not worse (e.g., <5% activity) than the wild-type human LPL (SEQ ID NO: 3). For example, the LPL polypeptide may exhibit activity that is similar to (e.g., within ±5% activity) or better (e.g., >5% activity) than the wild-type human LPL (SEQ ID NO: 3). Preferably, the LPL polypeptide may exhibit a $V_{max}$ of about 0.01-50 mmoles/h/mg in a [$^3$H]-triolein liposome activity assay and/or a $K_m$ value of about 0.01-1 μM.

LPL polypeptides disclosed herein may be substantially resistant to proteolytic cleavage (in particular, by proprotein convertase), e.g. LPL R324A (SEQ ID NO: 2). The LPL variants disclosed herein may have the advantage of increased stability when administered, especially in a subject having AP, e.g., where AP causes the release of a large amount of proteolytic enzymes from the gut into the plasma.

LPL polypeptide can be inactivated by proteolytic cleavage at the RAKR sequence located at amino acid positions 320-324 of SEQ ID NO: 3 by a proprotein convertase (PC). Thus, a useful LPL polypeptide for use in accordance with the present invention is one that is resistant to proteolytic cleavage by PC. For example, such a LPL polypeptide may comprise at least one point mutation that replaces, modifies or deletes any of the amino acids at the RAKR sequence located at amino acid positions 294-297 of SEQ ID NO: 1. The LPL polypeptide may have an amino acid substitution at position 297 of SEQ ID NO: 1, e.g., replacement with an alanine residue resulting in SEQ ID NO: 2 (referred to as LPL R324A herein). The LPL polypeptide may comprise an amino acid sequence having 80% or more identity (e.g. 85%, 90%, 91%, 92%, 93%, 94%, 95%, 96%, 97%, 98%, 99%, 99.5%, 99.8% or more) to SEQ ID NO: 2. Preferably, the LPL polypeptide comprises or consists of the amino acid sequence recited in SEQ ID NO: 2.

In some cases, the LPL polypeptide does not comprise or consist of the amino acid sequence recited in SEQ ID NO: 6, which is a S447X variant of wild-type human LPL.

The invention also encompasses the use of LPL polypeptides having single nucleotide polymorphisms (SNPs). For example, the human LPL gene locus is highly polymorphic and contains many SNPs in both coding and non-coding regions. For example, two SNPs in the coding DNA (cSNPs) occur at high frequencies in the general human population, and they concern point mutations in exon 2 and 6, causing the substitution of an aspartic acid to an asparagine residue at position 9 (D9N), and an asparagine to a serine residue at position 291 (N291S), respectively.

The invention is not limited to human LPL sequences, but rather encompasses such variants and homologs from other species (e.g. guinea pig, mouse, rat, chicken, baboon, ox, sheep, pig and fish), as well as non-natural variants. Standard search and alignment techniques can be used to identify the homolog of any particular LPL sequence. For example, cDNA clones for LPL have been isolated and sequenced from a number of species, including human, guinea pig, mouse, rat, chicken, baboon, ox, sheep, pig and fish. Homology between the primary protein sequences of all the mammalian species is in excess of 90% except in the case of the guinea pig, where homology is in the region of 80% compared to other mammals. Moreover, the available sequences from the LPL proteins can be used to design primers for amplification of homologous sequences from other species.

In general, suitable variants of a particular SEQ ID NO include its allelic variants, its polymorphic forms, its homologs, its orthologs, its paralogs, its mutants, etc.

Standard search and alignment techniques can be used to identify the homolog of any particular sequence from LPL in public sequence databases. Thus, for instance, LPL polypeptides used with the invention may, compared to the SEQ ID NOs herein, include one or more (e.g., 1, 2, 3, 4, 5, 6, 7, 8, 9, etc.) amino acid substitutions, such as conservative substitutions (i.e., substitutions of one amino acid with another which has a related side chain). Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The LPL polypeptides may also include one or more (e.g., 1, 2, 3, 4, 5, 6, 7, 8, 9, etc.) single amino acid deletions relative to the SEQ ID NO sequences. The LPL polypeptides may also include one or more (e.g., 1, 2, 3, 4, 5, 6, 7, 8, 9, etc.) insertions (e.g., each of 1, 2, 3, 4 or 5 amino acids) relative to the SEQ ID NO sequences.

Similarly, a LPL polypeptide used with the invention may comprise an amino acid sequence that:

(a) is identical (i.e. 100% identical) to a sequence disclosed in the sequence listing;

(b) shares sequence identity (e.g. 80%, 85%, 90%, 91%, 92%, 93%, 94%, 95%, 96%, 97%, 98%, 99%, 99.5% or more) with a sequence disclosed in the sequence listing;

(c) has 1, 2, 3, 4, 5, 6, 7, 8, 9 or 10 (or more) single amino acid alterations (deletions, insertions, substitutions), which may be at separate locations or may be contiguous, as compared to the sequences of (a) or (b); and (d) when aligned with a particular sequence from the sequence listing using a pairwise alignment algorithm, each moving window of x amino acids from N-terminus to C-terminus (such that for an alignment that extends top amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm, using default parameters (e.g., with Gap opening penalty=10.0, and with Gap extension penalty=0.5, using the EBLOSUM62 scoring matrix). This algorithm is conveniently implemented in the needle tool in the EMBOSS package.

Within group (c), deletions or substitutions may be at the N-terminus and/or C-terminus, or may be between the two termini. Thus a truncation is an example of a deletion. Truncations may involve deletion of up to 40 (or more) amino acids at the N-terminus and/or C-terminus N-terminus truncation can remove leader peptides e.g., to facilitate recombinant expression in a heterologous host. C-terminus truncation can remove anchor sequences e.g., to facilitate recombinant expression in a heterologous host. Preferably, the LPL polypeptide contains alterations which substantially retain desirable properties (e.g., $V_{max}$ of about 0.01-50 mmoles/h/mg in a [$^3$H]-triolein liposome activity assay and/or a $K_m$ value of about 0.01-1 μM).

In general, when a LPL polypeptide of the invention comprises a sequence that is not identical to a complete sequence from the sequence listing (e.g., when it comprises a sequence listing with <100% sequence identity thereto, or when it comprises a fragment thereof) it is preferred in each individual instance that the LPL polypeptide is at least capable of hydrolyzing plasma or serum TGs into a diacylglycerol and a carboxylate (e.g., a free fatty acid and monoglyceride/glycerol). Preferably, the LPL polypeptide is capable of hydrolyzing triglycerides in lipoproteins, such as those found in chylomicrons and very low-density lipoproteins (VLDL), into free fatty acids and monoglyceride/glycerol molecules. Preferably, the LPL polypeptide has similar enzyme kinetics as the known wild-type LPL. For example, the LPL polypeptide may have a $V_{max}$ of about 0.01-50 mmoles/h/mg (e.g. when triolein liposome is used as a substrate) and/or a $K_m$ value of about 0.01-1 μM (e.g. when triolein liposome is used as a substrate).

LPL Fragments

LPL is organized into two structurally distinct regions, consisting of a larger amino-terminal domain (SEQ ID NO: 4, which corresponds to residues 1-312 of SEQ ID NO: 1) and a smaller carboxy-terminal end (SEQ ID NO: 5, which corresponds to residues 313-448 of SEQ ID NO: 1) connected by a flexible peptide. The C-terminus is required for the binding to the lipoprotein substrate, whereas the N-terminal domain is the region responsible for catalysis.

Polypeptides used with the invention may omit either one of the domains. Thus, a useful polypeptide may comprise an amino acid sequence comprising a fragment of at least 'n' consecutive amino acids of SEQ ID NO: 1 (or variants thereof described herein), wherein 'n' is 50 or more (e.g. 55, 60, 70, 80, 90 or more), whilst retaining at least the lipoprotein substrate-binding function or the catalysis activity of LPL.

Preferred fragments comprise the catalysis active site in the N-terminal domain of SEQ ID NO: 1. Preferably, the LPL polypeptide comprises an amino acid sequence having 80% or more identity (e.g. 85%, 90%, 91%, 92%, 93%, 94%, 95%, 96%, 97%, 98%, 99%, 99.5%, 99.8% or more) to the amino acid sequence recited in SEQ ID NO: 4. Other preferred fragments lack one or more amino acids (e.g. 1, 2, 3, 4, 5, 6, 7, 8, 9, 10, 15, 20, 25 or more) from the N-terminus, while retaining at least the catalysis activity of LPL.

Preferred fragments comprise the lipoprotein substrate-binding site in the C-terminal domain of SEQ ID NO: 1. Preferably, the LPL polypeptide comprises an amino acid sequence having 80% or more identity (e.g. 85%, 90%, 91%, 92%, 93%, 94%, 95%, 96%, 97%, 98%, 99%, 99.5%, 99.8% or more) to the amino acid sequence recited in SEQ ID NO:

5. Other preferred fragments lack one or more amino acids (e.g. 1, 2, 3, 4, 5, 6, 7, 8, 9, 10, 15, 20, 25 or more) from the C-terminus, while retaining at least the lipoprotein substrate-binding function of LPL.

Hybrid Polypeptides

The invention may use a 'hybrid' polypeptide, which includes at least two LPL polypeptides of the invention (i.e. a dimer) expressed as a single polypeptide chain. An advantage of using a hybrid polypeptide is that a LPL polypeptide of the invention may be unstable or poorly expressed on its own, and this can be assisted by adding a suitable hybrid partner that overcomes the problem. For example, a hybrid polypeptide of the invention may consist of two monomers, each monomer being a LPL polypeptide comprising an amino acid sequence having 80% or more identity (e.g. 85%, 90%, 91%, 92%, 93%, 94%, 95%, 96%, 97%, 98%, 99%, 99.5%, 99.8% or more) to any of the amino acid sequences recited in SEQ ID NOs: 1-6. The two monomers may or may not be the same. The dimer may have a head-to-tail arrangement of the monomers. Alternatively, the dimer may have a head-to-head arrangement of monomers.

A hybrid polypeptide may also consist of monomers and/or oligomers of the fragments of LPL described above.

Hybrids consisting of amino acid sequences from different organisms can be useful. For example, a hybrid polypeptide may consist of the N-terminal domain of LPL from one species (e.g. human) and amino acid sequences comprising the C-terminal domain of LPL from another species (e.g. bovine).

Hybrid polypeptides can be represented by the formula $NH_2$-A-{—X-L-}$_n$-B—COOH, wherein: X is an amino acid sequence of a LPL polypeptide of the invention, as described above; L is an optional linker amino acid sequence; A is an optional N-terminal amino acid sequence; B is an optional C-terminal amino acid sequence; n is an integer of 2 or more (e.g., 2, 3, 4, 5, 6, etc.). Usually n is 2. The linker amino acid sequence L will typically be short (e.g., 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, or poly-glycine linkers. Other suitable linker amino acid sequences will be apparent to those skilled in the art.

The individual monomers within the hybrid (i.e. individual —X— moieties) may be from one or more species. Where n=2, for instance, $X_2$ may be from the same species as $X_1$ or from a different species. Where n=3, the species might be (i) $X_1=X_2=X_3$ (ii) $X_1=X_2\neq X_3$ (iii) $X_1\neq X_2=X_3$ (iv) $X_1\neq X_2\neq X_3$ or (v) $X_1=X_3\neq X_2$, etc.

Different hybrid polypeptides may be mixed together in a single formulation. The hybrid polypeptides can also be combined with polypeptides of the invention as described above. Usefully, these hybrid polypeptides are at least capable of hydrolyzing plasma or serum TGs into a diacylglycerol and a carboxylate (e.g., a free fatty acid and monoglyceride/glycerol). Preferably, the hybrid is capable of hydrolyzing triglycerides in lipoproteins, such as those found in chylomicrons and very low-density lipoproteins (VLDL), into free fatty acids and monoglyceride/glycerol molecules. Preferably, the hybrid has similar enzyme kinetics as the known wild-type LPL. For example, the LPL polypeptide may have a $V_{max}$ of about 0.01-50 mmoles/h/mg (e.g. when triolein liposome is used as a substrate) and/or a $K_m$ value of about 0.01-1 μM (e.g. when triolein liposome is used as a substrate).

LPL Polypeptides Used with the Invention

LPL polypeptides used with the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Preferably the invention uses LPL polypeptides that are glycosylated. The mature LPL may contain approximately 0-15% carbohydrate, and may have a molecular weight of about 50-60 kDa. The human wild-type LPL sequence contains three consensus sites for N-linked glycosylation (Asn-X-Ser, where X can be any amino acid) that are located at Asn-43, Asn-257 and Asn-359 of SEQ ID NO: 1. Experimental evidence suggests that N-linked glycosylation of LPL is important for its catalytic activity. Thus, a LPL polypeptide of the invention is preferably glycosylated. An exemplary glycosylated polypeptide may have approximately 9% carbohydrate, and/or a molecular weight of about 55 kDa.

In some embodiments, the LPL polypeptides used with the invention may be non-glycosylated.

Polypeptides used with the invention are preferably human polypeptides.

The LPL polypeptides used with the invention may be in the form of an oligomer. For example, the LPL polypeptide may be in the form of a dimer (e.g., homodimer), preferably a non-covalent dimer. In some embodiments, the LPL polypeptide may be in the form of a tetramer.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulphide bond formation, glycosylation, lipidation, acetylation, phosphorylation, or any other manipulation or modification, such as conjugation with a labelling component. Also included are, for example, polypeptides containing one or more analogs of an amino acid (including, for example, unnatural amino acids, etc.), as well as other modifications known in the art. Polypeptides can occur as single chains or associated chains.

The invention provides polypeptides comprising a sequence —P-Q- or -Q-P—, wherein: —P— is an amino acid sequence as defined above and -Q- is not a sequence as defined above i.e. the invention provides fusion proteins. Where the N-terminus codon of —P— is not ATG, but this codon is not present at the N-terminus of a polypeptide, it will be translated as the standard amino acid for that codon rather than as a Met. Where this codon is at the N-terminus of a polypeptide, however, it will be translated as Met. Examples of -Q- moieties include, but are not limited to, histidine tags (i.e. $His_n$ where n=3, 4, 5, 6, 7, 8, 9, 10 or more), one or more myc tag (i.e. SEQ ID NO: 7: EQKLISEEDL), maltose-binding protein, glutathione-S-transferase (GST).

In some embodiments, the present invention provides LPL polypeptides in a fusion protein configuration. For example, a suitable LPL polypeptide may be a fusion protein between an LPL domain and another domain or moiety that typically can facilitate a therapeutic effect of LPL by, for example, enhancing or increasing stability, potency and/or delivery of LPL, or reducing or eliminating immunogenicity, clearance, or toxicity. Such suitable domains or moieties for an LPL fusion protein include but are not limited to Fc domain, XTEN domain. In some embodiments, a suitable recombinant LPL protein contains an Fc domain or a portion thereof that binds to the FcRn receptor. As a non-limiting example, a suitable Fc domain may be derived from an immunoglobulin subclass such as IgG. In some embodiments, a suitable Fc domain is derived from IgG1, IgG2, IgG3, or IgG4. In some embodiments, a suitable Fc domain is derived from IgM, IgA, IgD, or IgE. Particularly suitable Fc domains include those derived from human or humanized antibodies. In some embodiments, a suitable Fc domain is a modified Fc portion, such as a modified human Fc portion with improved binding between Fc domain and the FcRn receptor resulting in prolonged serum half-life.

Exemplary Amino Acid Sequences for LPL Polypeptides

SEQ ID NO: 1

```
ADQRRDFIDIESKFALRTPEDTAEDTCHLIPGVAESVATCHFNHSSKTF
MVIHGWTVTGMYESWVPKLVAALYKREPDSNVIVVDWLSRAQEHYPVSA
GYTKLVGQDVARFINWMEEEFNYPLDNVHLLGYSLGAHAAGIAGSLTNK
KVNRITGLDPAGPNFEYAEAPSRLSPDDADFVDVLHTFTRGSPGRSIGI
QKPVGHVDIYPNGGTFQPGCNIGEAIRVIAERGLGDVDQLVKCSHERSI
HLFIDSLLNEENPSKAYRCSSKEAFEKGLCLSCRKNRCNNLGYEINKVR
AKRSSKMYLKTRSQMPYKVFHYQVKIHFSGTESETHTNQAFEISLYGTV
AESENIPFTLPEVSTNKTYSFLIYTEVDIGELLMLKLKWKSDSYFSWSD
WWSSPGFAIQKIRVKAGETQKKVIFCSREKVSHLQKGKAPAVFVKCHDK
SLNKKSG
```

SEQ ID NO: 2

```
ADQRRDFIDIESKFALRTPEDTAEDTCHLIPGVAESVATCHFNHSSKTF
MVIHGWTVTGMYESWVPKLVAALYKREPDSNVIVVDWLSRAQEHYPVSA
GYTKLVGQDVARFINWMEEEFNYPLDNVHLLGYSLGAHAAGIAGSLTNK
KVNRITGLDPAGPNFEYAEAPSRLSPDDADFVDVLHTFTRGSPGRSIGI
QKPVGHVDIYPNGGTFQPGCNIGEAIRVIAERGLGDVDQLVKCSHERSI
HLFIDSLLNEENPSKAYRCSSKEAFEKGLCLSCRKNRCNNLGYEINKVR
AKASSKMYLKTRSQMPYKVFHYQVKIHFSGTESETHTNQAFEISLYGTV
AESENIPFTLPEVSTNKTYSFLIYTEVDIGELLMLKLKWKSDSYFSWSD
WWSSPGFAIQKIRVKAGETQKKVIFCSREKVSHLQKGKAPAVFVKCHDK
SLNKKSG
```

SEQ ID NO: 3

```
MESKALLVLTLAVWLQSLTASRGGVAAADQRRDFIDIESKFALRTPEDT
AEDTCHLIPGVAESVATCHFNHSSKTFMVIHGWTVTGMYESWVPKLVAA
LYKREPDSNVIVVDWLSRAQEHYPVSAGYTKLVGQDVARFINWMEEEFN
YPLDNVHLLGYSLGAHAAGIAGSLTNKKVNRITGLDPAGPNFEYAEAPS
RLSPDDADFVDVLHTFTRGSPGRSIGIQKPVGHVDIYPNGGTFQPGCNI
GEAIRVIAERGLGDVDQLVKCSHERSIHLFIDSLLNEENPSKAYRCSSK
EAFEKGLCLSCRKNRCNNLGYEINKVRAKRSSKMYLKTRSQMPYKVFHY
QVKIHFSGTESETHTNQAFEISLYGTVAESENIPFTLPEVSTNKTYSFL
IYTEVDIGELLMLKLKWKSDSYFSWSDWWSSPGFAIQKIRVKAGETQKK
VIFCSREKVSHLQKGKAPAVFVKCHDKSLNKKSG
```

SEQ ID NO: 4

```
ADQRRDFIDIESKFALRTPEDTAEDTCHLIPGVAESVATCHFNHSSKTF
MVIHGWTVTGMYESWVPKLVAALYKREPDSNVIVVDWLSRAQEHYPVSA
GYTKLVGQDVARFINWMEEEFNYPLDNVHLLGYSLGAHAAGIAGSLTNK
```

-continued

```
KVNRITGLDPAGPNFEYAEAPSRLSPDDADFVDVLHTFTRGSPGRSIGI
QKPVGHVDIYPNGGTFQPGCNIGEAIRVIAERGLGDVDQLVKCSHERSI
HLFIDSLLNEENPSKAYRCSSKEAFEKGLCLSCRKNRCNNLGYEINKVR
AKRSSKMYLKTRSQMPYK
```

SEQ ID NO: 5

```
VFHYQVKIHFSGTESETHTNQAFEISLYGTVAESENIPFTLPEVSTNKT
YSFLIYTEVDIGELLMLKLKWKSDSYFSWSDWWSSPGFAIQKIRVKAGE
TQKKVIFCSREKVSHLQKGKAPAVFVKCHDKSLNKKSG
```

SEQ ID NO: 6

```
ADQRRDFIDIESKFALRTPEDTAEDTCHLIPGVAESVATCHFNHSSKTF
MVIHGWTVTGMYESWVPKLVAALYKREPDSNVIVVDWLSRAQEHYPVSA
GYTKLVGQDVARFINWMEEEFNYPLDNVHLLGYSLGAHAAGIAGSLTNK
KVNRITGLDPAGPNFEYAEAPSRLSPDDADFVDVLHTFTRGSPGRSIGI
QKPVGHVDIYPNGGTFQPGCNIGEAIRVIAERGLGDVDQLVKCSHERSI
HLFIDSLLNEENPSKAYRCSSKEAFEKGLCLSCRKNRCNNLGYEINKVR
AKRSSKMYLKTRSQMPYKVFHYQVKIHFSGTESETHTNQAFEISLYGTV
AESENIPFTLPEVSTNKTYSFLIYTEVDIGELLMLKLKWKSDSYFSWSD
WWSSPGFAIQKIRVKAGETQKKVIFCSREKVSHLQKGKAPAVFVKCHDK
SLNKK
```

Expression and Purification

LPL polypeptides used with the invention can be prepared by various means (e.g. recombinant expression, purification from cell culture, chemical synthesis, etc.). For example, the LPL polypeptide may be expressed in the presence of dextran and sulfate.

The expression of the LPL polypeptides of the invention usually takes place in a mammalian host. The invention may use a heterologous host for expression (recombinant expression). The heterologous host may be prokaryotic (e.g., a bacterium) or eukaryotic. Preferably, the heterologous host is eukaryotic, for example, human cells (e.g. HT1080 cells, HEK293 cells), and hamster cells (e.g. CHO cells and variants thereof). In some cases, the heterologous host is a plant cell. In some cases, the heterologous host is an insect cell.

Generally, LPL polypeptides of the invention are prepared by recombinant expression. For example, a nucleic acid molecule (e.g. a vector) encoding a LPL polypeptide of the invention may be stably or transiently introduced into the cells to stably or transiently express the LPL polypeptide. Preferably, the nucleic acid molecule (e.g. a vector) encoding the LPL polypeptide is stably introduced into the cells for stable expression of the LPL polypeptide.

The inventors have found that LMF1 plays a role in LPL folding, dimer formation, and secretion, thereby giving a higher titer in conditioned medium (see results of ELISA experiments shown in FIG. 1). The LPL expression level from HT1080 cells increased 20-25 fold following co-expression with LMF1. This may promote assembly and secretion of the LPL protein, thereby giving a significantly higher yield. Thus, the invention preferably uses a cell that expresses (e.g., prepared by recombinant expression) a polypeptide of the invention and LMF1. The expression can be stable or transient. Cells suitable for this can be prepared in various ways.

For example, a method according to this aspect of the invention involves transfecting a cell with nucleic acids encoding: (a) a LPL polypeptide of the invention and (b) LMF1, to express the LPL polypeptide and LMF1, respectively. The nucleic acids encoding the LPL polypeptide of the invention and LMF1 may be present in the same or different expression vectors. The nucleic acids encoding (a) a LPL polypeptide of the invention and (b) LMF1 may be transfected simultaneously or in series.

For example, such a method may involve: (i) transfecting a cell with a nucleic acid molecule (e.g. a vector) encoding LMF1 to express LMF1, and (ii) transfecting the cell with a nucleic acid molecule (e.g. a vector) encoding a LPL polypeptide of the invention to express that polypeptide. In one embodiment, step (i) is carried out before (ii). In another embodiment, step (i) is carried out after step (ii). In another embodiment, steps (i) and (ii) are carried out simultaneously.

For example, such a method may involve transfecting a cell with a nucleic acid molecule (e.g. a vector) encoding a LPL polypeptide of the invention, wherein the cell stably expresses LMF1. In this example, the cell may have been previously transfected with a nucleic acid molecule (e.g. a vector) encoding LMF1 to express LMF1.

Another method involves transfecting a cell with a nucleic acid molecule (e.g. a vector) encoding LMF1, wherein the cell stably expresses a LPL polypeptide of the invention. In this example, the cell may have been previously transfected with a nucleic acid molecule (e.g. a vector) encoding the LPL polypeptide to express the LPL polypeptide.

Transient gene expression in cells can be carried out by various techniques, including the calcium phosphate or calcium chloride co-precipitation, lipofection, electroporation, viral-mediated transfection methods etc. Suitable methods for transfecting host cells can be found in common laboratory manuals.

Techniques for stable gene expression in cells are also known in the art. For example, a nucleic acid molecule encoding the LPL polypeptide may be stably introduced into the cells (e.g. by chromosomal integration). For example, the cells can be transfected with expression vectors which may contain origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

The invention also encompasses inducible gene expression systems, e.g. doxycycline-inducible expression system.

LPL polypeptides of the invention can be chemically synthesized using standard techniques. Automated peptide synthesizers are commercially available (e.g. Advanced ChemTech Model 396; Milligen/Biosearch 9600). Polypeptides may be dimerised via a disulfide bridge formed by oxidation of the cysteins. Following HPLC purification dimer formation may be verified, by mass spectrometry.

LPL polypeptides used with the invention may be purified by HPLC. The LPL polypeptides may be purified using a 2-column purification process (for example, eButyl-Heparin) wherein the capture column may be any hydrophobic interacting column (HIC) (e.g., octyl, phenyl, butyl). The purification process may include additional column for removing cell culture residuals such as host cell proteins and host cell DNA.

The purified LPL polypeptides may be analyzed and assayed for activity in accordance with standard methods. For example, the purified product may be analyzed by mass spectrometry and additional analytical methods including those capable of analyzing glycan heterogeneity (e.g. 2-aminobenzamide hydrophilic-interaction liquid chromatography (2AB/HILIC)), charge heterogeneity (e.g. imaged capillary isoelectric focusing (iCE)), variation in the multimeric state of the molecule (e.g. size exclusion (SE)-HPLC) and product fragments (e.g. SDS-CE).

LPL polypeptides of the invention are preferably provided in purified or substantially purified form i.e. substantially free from other polypeptides (e.g., free from naturally-occurring polypeptides), particularly from other host cell polypeptides, and are generally at least about 50% pure (by weight), and usually at least about 90% pure, preferably about ≥95% pure. Hence, less than about 50%, and more preferably less than about 10% (e.g., 5%) of a composition is made up of other expressed polypeptides. Thus the LPL polypeptides of the invention in the compositions are separated from the whole organism with which the LPL polypeptide is expressed.

Pharmaceutical Compositions

Pharmaceutical compositions of the invention should be pharmaceutically acceptable. Such compositions will usually include components in addition to the antigens e.g., they typically include one or more pharmaceutically acceptable carrier(s) and/or excipient(s). A thorough discussion of such components is available in reference Gennaro, 2000, Remington: The Science and Practice of Pharmacy. 20th edition.

Depending on the route of administration, the peptides of the invention may be coated in a material to protect said ingredients from the action of enzymes, acids or other natural conditions. Compositions will generally be in aqueous form. Suitable compositions include aqueous solutions or dispersions and powders for the extemporaneous preparation of solutions or dispersion. The compositions are stable under the conditions of manufacture and storage and are preserved against the contaminating action of microorganisms such as bacteria and fungi. The aqueous solutions are sterile and fluid to the extent that the solution may readily be placed in a syringe.

The carrier may be a solvent or dispersion medium containing, for example, water, ethanol, polyol (for example, monoglyceride/glycerol, propylene glycol, and polyethylene glycol, and the like), suitable mixtures thereof, and vegetable oils. The fluidity may be maintained, for example, by the use of a coating such as lecithin, by the maintenance of the required particle size in the case of dispersion and by the use of surfactants. The preventions of the action of microorganisms may be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions may be brought about by the use in the compositions of agents delaying absorption, for example, aluminum monostearate and gelatin.

Solutions are prepared by incorporating the peptides of the invention in the required amount in the appropriate solvent with various of the other ingredients enumerated above, as required, followed by filter sterilization.

Generally, dispersions are prepared by incorporating the various polypeptides of the invention into vehicle which contains the basic dispersion medium and the required other ingredients from those enumerated above. Dispersions may also be prepared in monoglyceride/glycerol, liquid polyethylene glycols, and mixtures thereof and in oils. Under ordinary conditions of storage and use, these preparations contain a preservative to prevent the growth of microorganisms.

In the case of powders for the preparation of solutions, the preferred methods of preparation are vacuum drying and the freeze-drying (lyophilization) technique which yield a powder of the peptides plus any additional desired ingredient from previously sterile-filtered solution thereof. Thus the invention also provides a lyophilizate of an aqueous composition of the invention. This is prepared by lyophilizing an aqueous composition of the invention. It can then be reconstituted with aqueous material to provide an aqueous immunogenic composition of the invention. If the material is reconstituted with a smaller volume of material than before lyophilization then these materials will be present in more concentrated form.

Of course, any material used in preparing any dosage unit form should be pharmaceutically pure and substantially non-toxic in the amounts employed.

A pharmaceutical composition comprising a polypeptide of the invention preferably contains less than 10 ng (preferably less than ing, and more preferably less than 100 pg) of residual host cell DNA per dose, although trace amounts of host cell DNA may be present.

The peptides of the invention may be incorporated into sustained-release preparations and formulations.

The invention also provides a kit or composition of the invention for use as a medicament in enzyme therapy.

Methods of Treatment

LPL polypeptides and compositions of the invention are suitable for administration to subjects. Such LPL polypeptides and compositions may be useful in treating hyperlipidemia and hyperlipidemia-related conditions, including conditions that are secondary to or exacerbated by hyperlipidemia, e.g. hypertriglyceridemia (HTG), dyslipidemia, chlymicroemia, hypercholesterolemia, dysbetalipoproteinemia, mixed hyperlipoprotienemia and/or combined hyperlipidemia. For example, the invention provides a LPL polypeptide or a composition for use in treating HTG and its associated diseases, in a subject. The HTG-associated diseases include diseases that are secondary to and/or are exacerbated by HTG, e.g., AP, cardiovascular disease, metabolic disorders, endocrine disorders, and fat embolism syndrome.

Preferably, the invention provides a method of treating AP in a subject, comprising the step of administering to the subject an effective amount of a LPL polypeptide or a composition of the invention. The invention also provides the use of a LPL polypeptide or a composition of the invention in the preparation of a medicament for the treatment of AP in a subject. The invention can be used to treat AP at the time of onset of AP or at any point during the course of the disease.

The subject may have hyperlipidemia, e.g. hypertriglyceridemia (HTG), dyslipidemia, chlymicroemia, hypercholesterolemia, dysbetalipoproteinemia, mixed hyperlipoproteinemia and/or combined hyperlipidemia. Preferably, the subject may have HTG.

The serum triglyceride level in the subject in need of treatment may exceed about 150 mg/dl, about 200 mg/dl, about 300 mg/dl, about 400 mg/dl, about 500 mg/dl, about 600 mg/dl, about 600 mg/dl, about 700 mg/dl, about 800 mg/dl, about 900 mg/dl, or about 1000 mg/dl.

The AP may be secondary to or exacerbated by hyperlipidemia, e.g. hypertriglyceridemia (HTG), dyslipidemia, chlymicroemia, hypercholesterolemia, dysbetalipoproteinemia, mixed hyperlipoprotienemia and/or combined hyperlipidemia. Preferably, the AP is secondary to HTG. In other cases, the AP is exacerbated by HTG.

The subject may have interstitial edematous AP or necrotizing AP.

The subject may have mild, moderate or severe AP.

After administration of the LPL polypeptides of the invention, the plasma TG level in the subject preferably decreases below about 2000 mg/dl, about 1000 mg/dl, or about 500 mg/dl, or about 150 mg/dl. In some cases, the plasma TG level in the subject decreased by about 15%, about 20%, about 30%, about 40%, about 50%, about 60%, about 70%, about 80% or more, after administration of the LPL polypeptides disclosed herein. Preferably, the decrease in TG level may be observed after 1 hour, 6 hour, 12 hours, 1 day, or 1 week. Assessment of triglyceride levels in the plasma and serum is well known in the art.

Preferably, administration of the LPL polypeptides of the invention may lead to an improvement in AP or other diseases disclosed herein. Potential endpoints that may be affected include hospital length of stay, ICU length of stay, mortality rate, incidence of complications, organ dysfunction, need for invasive treatment, decrease in severity scores and/or markers of inflammation, time to resolution of pain, cost of hospitalization, relapses or recurrent AP, pancreatic insufficiency/glucose intolerance, pain, clinician reported outcomes, quality of life measures and other markers of clinical improvement.

Prophylactic Treatment

LPL polypeptides and compositions of the invention are also useful in prophylactic treatment of hyperlipidemia and hyperlipidemia-related conditions, including conditions that are secondary to or exacerbated by hyperlipidemia, e.g. hypertriglyceridemia (HTG), dyslipidemia, chlymicroemia, hypercholesterolemia, dysbetalipoproteinemia, mixed hyperlipoprotienemia and/or combined hyperlipidemia. Prophylactic treatment refers to treatment before onset or reoccurrence of the disease to prevent, inhibit or reduce the occurrence or reoccurrence of the disease.

For example, the invention provides a LPL polypeptide or a composition for use in preventing, inhibiting and/or reducing the occurrence of HTG and its associated diseases, in a subject. The HTG-associated diseases include diseases that are secondary to and/or are exacerbated by HTG, e.g., AP, cardiovascular disease, metabolic disorders, endocrine disorders, and fat embolism syndrome.

AP patients following hospital discharge are typically advised to maintain low TG levels. However, the patients have a high recurrent AP rate (20-60%) and this suggests that the current standard of care to maintain TG levels is ineffective. The invention is also suited for prophylactic treatment of AP.

Thus, the invention also provides a LPL polypeptide (e.g., human wild-type LPL, or its variant) for use in the prevention, inhibition and/or reduction in the occurrence or reoccurrence of AP in a subject. The invention also provides a method of preventing, inhibiting and/or reducing the occurrence or reoccurrence of AP in a subject, comprising the step of administering to the mammal an effective amount of the LPL polypeptide of the invention. The invention also provides the use of the LPL polypeptide of the invention in the preparation of a medicament for the prevention, inhibition and/or reduction in the occurrence or reoccurrence of AP in a subject.

Typically, the subject's plasma or serum triglyceride level is maintained below about 150 mg/dl, below about 500 mg/dl, below about 1000 mg/dl, or below about 2000 mg/dl.

For example, a subject at risk of AP who previously had an attack of HTGAP can be prophylactically treated according to the method of the present invention prior to the onset or recurrence of AP.

The peptides of the invention are not suitable solely for these groups, however, and may be used more generally in a population.

Administration of LPL

The invention includes administering an effective amount of a LPL polypeptide of the invention to the subject. An effective amount is an amount sufficient to reduce, prevent, or inhibit the effects of AP, or other diseases disclosed herein, in the subject.

Preferably, the LPL is not administered in the form of a nucleic acid, e.g., in a gene therapy vector (e.g., using an adeno-associated virus). Preferably, the invention does not include administering to a subject a nucleic acid (e.g., in a gene therapy vector, such as using an adeno-associated virus) that encodes the amino acid sequence recited in SEQ ID NO: 6 (LPL S447X).

In a preferred embodiment, the therapeutic amount ranges from about 1 μg to about 100 mg per kg of body weight per day. In some embodiment, the LPL polypeptide variant, R324A, exhibits a $V_{max}$=153±14 μmoles FA/min/mg and $K_m$=0.28±0.07 μM in a [$^3$H]-triolein liposome activity assay, which is within the values reported in the literature for human LPL using the same activity assay. LPL polypeptides used in accordance with the invention preferably possess an activity with a $V_{max}$ of 0.01-50 mmoles FA/hr/mg and a $K_m$ of 0.01-1 uM.

The invention may use the LPL polypeptides at a concentration of ≤8, ≤9, ≤10 or ≤11, ≤12 mg/kg, most suitably, at a dose of ≤100 mg/kg, or maximum feasible dose (MFD).

LPL polypeptides or compositions of the invention will be administered directly to a patient. A practical advantage is that the peptide may be administered in a convenient manner such as by the oral, intravenous, intramuscular, intravenous, intranasal, intradermal, subcutaneous, or suppository routes. The peptides of the invention may also be administered parenterally or intraperitoneally, or by other methods disclosed herein.

The administration route is preferably intravenous. Preferably, a LPL polypeptide of the invention may be administered at a dose of ≤100 mg/kg by intravenous route or MFD.

The administration is preferably subcutaneous. Preferably, a LPL polypeptide of the invention may be administered at a concentration of at a concentration of ≤100 mg/kg by subcutaneous route or MFD.

The LPL polypeptides or compositions of the invention may be administered by continuous infusion. The LPL polypeptides or compositions of the invention may be administered by a single injection (e.g., a bolus injection), or by multiple repeated doses.

The dosage regimen may be adjusted to provide the optimum therapeutic response. Dosage can be by a single dose schedule or a multiple dose schedule. For example, several divided doses may be administered daily. Multiple doses may be administered at least 1 week apart (e.g., about 2 weeks, about 3 weeks, about 4 weeks, about 6 weeks, about 8 weeks, about 10 weeks, about 12 weeks, about 16 weeks, etc.). The dose may be proportionally reduced as indicated by the exigencies of the therapeutic situation.

Preferably the subject is a mammal Preferably the subject is a human. Suitable examples of mammals other than humans include, for example, rabbits, rats, mice, horses, minks, goats, or primates.

General

The practice of the present invention will employ, unless otherwise indicated, conventional methods of chemistry, biochemistry, molecular biology, immunology and pharmacology, within the skill of the art. Such techniques are explained fully in the literature.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g., for correction, or to add more annotation or information) then it receives a new GI number. Thus the sequence associated with a given GI number is never changed.

The term "comprising" encompasses "including" as well as "consisting" e.g. a composition "comprising" X may consist exclusively of X or may include something additional e.g., X+Y.

The word "substantially" does not exclude "completely" e.g., a composition which is "substantially free" from Y may be completely free from Y. Where necessary, the word "substantially" may be omitted from the definition of the invention.

The term "about" in relation to a numerical value x means, for example, x±10%.

References to a percentage sequence identity between two amino acid sequences means that, when aligned, that percentage of amino acids are the same in comparing the two sequences. This alignment and the percent homology or sequence identity can be determined using software programs known in the art. A preferred alignment is determined by the Smith-Waterman homology search algorithm using an affine gap search with a gap open penalty of 12 and a gap extension penalty of 2, BLOSUM matrix of 62.

Where a compound is administered to the body as part of a composition then that compound may alternatively be replaced by a suitable prodrug.

EXAMPLES AND EMBODIMENTS

LPL Expression and Purification

This experiment aimed to improve LPL titer. LPL was expressed in either HT1080 cells or a stable HT1080 cell line that co-expresses lipase maintaining factor 1 (LMF1) in the presence of dextran sulfate. The LPL was then purified from the conditioned medium using a 2-column purification process (Butyl-Heparin). A human LPL variant, LPL R324A (SEQ ID NO: 2), was used in the experiment.

The amount of LPL expressed from HT1080 cells co-expressing LMF1 was measured by ELISA, and the results are shown in FIG. 1. The titer of LPL R324A obtained using an HT1080 stable cell line was approximately 1 mg/L. In contrast, the stable cell line that co-expresses LMF1 provided >20-fold increase in LPL R324A titer, giving a titer of about 25 mg/L.

Such results indicated that LMF1 can play a role in LPL folding, dimer formation, and secretion, yielding a significantly higher LPL titer in conditioned medium.

Specific Activity

Figure 2A:
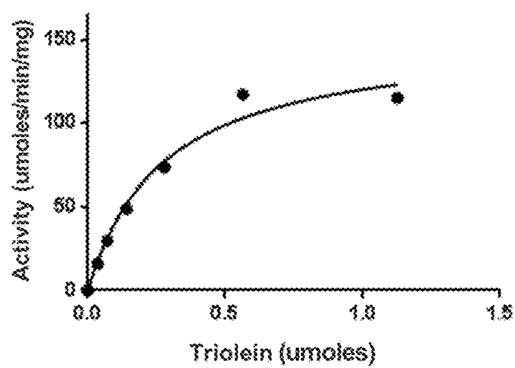
FIGS. 2A and 2B shows the enzymatic properties of the LPL using Michaelis-Menten kinetics (FIG. 2A) and Eadie-Hofstee kinetics (FIG. 2B).
Figure 2B:
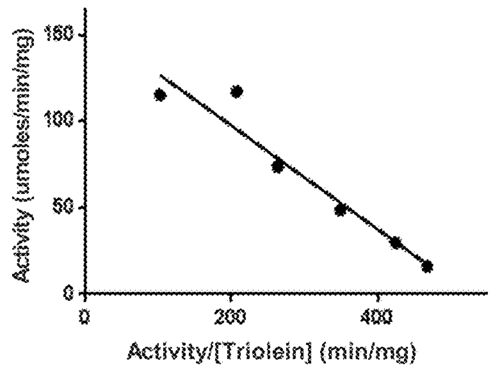

The lipolytic activity of the LPL R324A was measured with 3[H]-triolein liposome as a substrate. The results are shown in FIG. 2. The specific lipolytic activity of the LPL was 4-10 mmoles/hr/mg, which is within the values reported in the literature for human LPL.

Enzymatic Properties

The enzymatic properties of LPL R324A LPL were measured and the results are shown in FIG. 2 using a $[^3H]$-triolein liposome substrate. Following Michaelis-Menten kinetics (FIG. 3A), the recombinant LPL has: Vmax=153±14 μmoles FA/min/mg, Km=0.28±0.07 μM and $R^2$=0.98. Following Eadie-Hofstee kinetics (FIG. 3B), the recombinant LPL has: Vmax=158±14 μmoles FA/min/mg, Km=0.30±0.04 μM and $R^2$=0.92.

LPL Activity Ex Vivo

This experiment aims to investigate whether exogenous LPL is active in human plasma. This experiment also aims to investigate whether LPL R324A remains active in plasma obtained from individuals with HTGAP.

Also, AP causes the release of proteolytic enzymes from the gut into the plasma, so it was unclear whether LPL would remain active in the presence of the proteolytic enzymes. Plasma samples were obtained from HTG patients with or without AP. Recombinant LPL R324A was added to the samples, and the concentrations of TGs and FFAs were measured over time. It was found that LPL R324A rapidly hydrolyzed TGs with a concomitant increase in FFAs in both HTG and HTGAP patients (FIGS. 3-4).

There is a dose-dependent hydrolysis of TGs as demonstrated by the increase in FFA concentration following treatment with increasing amounts of LPL (FIG. 5).

Additionally, LPL polypeptide is also capable of rapidly hydrolyzing triglycerides in non-human primate (NHP) plasma with HTG. This was demonstrated by incubating an isolated LPL polypeptide variant R324A in plasma samples obtained from 11 HTG NHPs (baseline TGs 1566±352 mg/dL, range 352-5360 mg/dL) and assessing changes in non-esterified fatty acid (NEFA) concentrations. FIG. 6 shows time-courses of NEFA concentrations following incubation of LPL for all 11 HTG NHPs. In all samples, LPL led to a rapid hydrolysis of triglycerides as demonstrated by a rapid increase in NEFA concentrations.

It was surprising that the exogenous LPL was active in human plasma and that the LPL remained active in plasma from HTG patients with or without AP. This therefore suggests that LPL could be effective in lowering TG levels, e.g. by hydrolyzing triglycerides in lipoproteins, such as those found in chylomicrons and very low-density lipoproteins (VLDL), in AP patients.

LPL Activity In Vivo

LPL has been reported to have a short half-life (6-30 min), so it was unclear whether exogenously administered LPL would be sufficient to reduce TG levels in vivo.

The ob/ob mouse model was used for this study. LPL R324A was administered IV at doses of 0.1 mg/kg, 0.5 mg/kg and 1 mg/kg. As negative controls, mice were injected with the vehicle only (20 MM TrisCl, pH8, 5 mM $CaCl_2$, 30% glycerol, 1.5M NaCl).

FIG. 7 shows a >85% drop in serum triglyceride levels ($p<0.001$) following IV administration of 1 mg/kg recombinant in ob/ob mice. Despite the large drop in serum TGs, serum FFA concentration remained unchanged. FFAs are rapidly transported to target tissues by albumin and thus our findings are consistent with the rapid clearance of FFAs as reported in the literature. FIG. 8 shows that TG hydrolysis in ob/ob mice is dose-dependent. Thus, recombinant LPL has functional activity when administered in vivo.

It will be understood that the invention has been described by way of example only and modifications may be made whilst remaining within the scope and spirit of the invention.

The invention claimed is:

1. A method of treating hypertriglyceridemia comprising administering a LPL polypeptide to a subject in need of treatment, wherein the LPL polypeptide comprises or consists of the amino acid of SEQ ID NO: 2.

2. The method of claim 1, wherein the LPL polypeptide is substantially resistant to proteolytic cleavage by proprotein convertase.

3. The method of claim 1, wherein the hypertriglyceridemia is associated with acute pancreatitis, cardiovascular disease, a metabolic disorder, an endocrine disorder, or fat embolism syndrome.

4. The method of claim 1, wherein the serum or plasma triglyceride level in the subject exceeds about 150 mg/dl.

5. The method of claim 1, wherein the LPL polypeptide exhibits a $V_{max}$ of about 0.01-50 mmoles FA/hr/mg in a [$^3$H]-triolein liposome activity assay and/or a $K_m$ value of about 0.01-1 μM.

6. The method of claim 1, wherein the LPL polypeptide is administered intravenously.

7. The method of claim 6, wherein the LPL polypeptide is administered by continuous infusion or by bolus injection.

8. The method of claim 1, wherein the LPL polypeptide is administered as a single dose or multiple doses.

9. The method of claim 1 wherein the LPL polypeptide is glycosylated.

10. The method of claim 1, wherein the LPL polypeptide is non-glycosylated.

11. The method of claim 1, wherein the LPL polypeptide is in aqueous form.

12. The method of claim 1, wherein the LPL polypeptide is reconstituted from a lyophilized form.

13. The method of claim 1, wherein the subject is suffering from acute pancreatitis.

14. The method of claim 13, wherein the acute pancreatitis is secondary to or exacerbated by hypertriglyceridemia.

* * * * *